(12) United States Patent
Bradley

(10) Patent No.: US 10,661,119 B2
(45) Date of Patent: May 26, 2020

(54) AUTONOMOUS SAFETY SYSTEM FOR A TREADMILL

(71) Applicant: James P. Bradley, Dallas, TX (US)

(72) Inventor: James P. Bradley, Dallas, TX (US)

( * ) Notice: Subject to any disclaimer, the term of this patent is extended or adjusted under 35 U.S.C. 154(b) by 0 days.

(21) Appl. No.: 15/966,280

(22) Filed: Apr. 30, 2018

(65) Prior Publication Data

US 2018/0243611 A1    Aug. 30, 2018

(51) Int. Cl.

| | |
|---|---|
| *A63B 24/00* | (2006.01) |
| *A63B 22/02* | (2006.01) |
| *A61B 5/107* | (2006.01) |
| *A61B 5/11* | (2006.01) |
| *A61B 5/00* | (2006.01) |
| *A63B 71/00* | (2006.01) |

(52) U.S. Cl.
CPC ........ *A63B 24/0087* (2013.01); *A61B 5/0077* (2013.01); *A61B 5/1072* (2013.01); *A61B 5/1079* (2013.01); *A61B 5/1117* (2013.01); *A61B 5/1128* (2013.01); *A63B 22/025* (2015.10); *A63B 71/0054* (2013.01); *A63B 2024/0093* (2013.01); *A63B 2071/0081* (2013.01); *A63B 2220/05* (2013.01); *A63B 2220/805* (2013.01); *A63B 2220/806* (2013.01); *A63B 2220/89* (2013.01); *A63B 2230/625* (2013.01)

(58) Field of Classification Search
CPC ............ A63B 24/0087; A63B 71/0054; A63B 22/025; A63B 2071/0081; A63B 2024/0093; A63B 2230/625; A63B 2220/89; A63B 2220/805; A63B 2220/05; A63B 2220/806; A61B 5/1128; A61B 5/1117; A61B 5/1079; A61B 5/1072; A61B 5/0077; A61B 2503/10
See application file for complete search history.

(56) References Cited

U.S. PATENT DOCUMENTS

| | | | |
|---|---|---|---|
| 4,227,487 A | 10/1980 | Davis | |
| 5,314,391 A | 5/1994 | Potash et al. | |

(Continued)

FOREIGN PATENT DOCUMENTS

| | | |
|---|---|---|
| CN | 201283189 Y | 8/2009 |
| CN | 202538245 U | 11/2012 |

(Continued)

OTHER PUBLICATIONS technogym.com, Jog Now, printed Dec. 16, 2015.

(Continued)

*Primary Examiner* — Loan B Jimenez
*Assistant Examiner* — Shila Jalalzadeh Abyaneh
(74) *Attorney, Agent, or Firm* — Terrile, Cannatti & Chambers; Michael Rocco Cannatti

(57) ABSTRACT

A treadmill safety control system, method, and apparatus are described for operating an exercise treadmill by enabling a treadmill motor to start moving the treadmill belt after an initial height of the user on the treadmill belt is measured, and then continually measuring a current height of the user on the treadmill belt for evaluation against the initial height so that a first treadmill motor control signal is generated to stop the treadmill motor from moving the treadmill belt when the current height is lower than the initial height by a minimum height threshold.

16 Claims, 4 Drawing Sheets

(56) References Cited

U.S. PATENT DOCUMENTS

| | | | |
|---|---|---|---|
| 5,368,532 A * | 11/1994 | Farnet | A63B 22/02 482/5 |
| 6,572,512 B2 | 6/2003 | Anderson et al. | |
| 6,733,423 B1 | 5/2004 | Chang | |
| 7,344,481 B2 | 3/2008 | Watterson et al. | |
| 7,713,172 B2 | 5/2010 | Watterson et al. | |
| 8,480,541 B1 | 7/2013 | Brunts | |
| 9,870,622 B1 * | 1/2018 | Lu | G06T 7/251 |
| 2006/0291694 A1 * | 12/2006 | Venetianer | G06K 9/00369 382/103 |
| 2007/0004562 A1 | 1/2007 | Pan et al. | |
| 2009/0036272 A1 * | 2/2009 | Yoo | A63B 22/0257 482/7 |
| 2011/0144542 A1 | 6/2011 | Jin et al. | |
| 2017/0065849 A1 * | 3/2017 | Konishi | A61B 5/6828 |

FOREIGN PATENT DOCUMENTS

| | | | |
|---|---|---|---|
| CN | 103623541 A | | 3/2014 |
| CN | 206473713 | * | 9/2017 |
| WO | WO 2010150260 A1 | | 12/2010 |

OTHER PUBLICATIONS eagleswingequine.com, Treadmill Rehabilitation, Conditioning and Warm-up, Horse Gym 2000, printed May 19, 2015.
doubledtrailers.com, Improve Fitness and Evaluate Problems with a Horse Treadmill, printed Jan. 29, 2018.
Michal Kepski et al., Human Fall Detection by Mean Shift Combined with Depth Connected Components, Int'l Conference on Computer Vision and Graphics (ICCVG) 2012, vol. 7594 of the series Lecture Notes in Computer Science, Springer, Berlin, Heidelberg, (Excerpt).
Michael E. Miller, Dave Goldberg's death points to rise and risks of treadmills in era of smartphones, smh.com. AU, Lifestyle, Health & Wellness, printed Apr. 13, 2018.
technogym.com, Excite Run 1000, printed Apr. 13, 2018.
Jeffrey B. Friedrich et al., Pediatric Hand Friction Burns from Treadmill Contact, American Association for Hand Surgery (2007) 2:188-193.
horse-gym-2000.net, Horse Gym 2000, printed Apr. 13, 2018.
Lenny Bernstein, How to safely use a treadmill (It's not as easy as you think), The Washington Post, May 5, 2015.
Wenjuan Gong et al., Human Pose Estimation from Monocular Images: A Comprehensive Survey, mdpi.com, Sensors 2016.

* cited by examiner

AUTONOMOUS SAFETY SYSTEM FOR A TREADMILL

BACKGROUND OF THE INVENTION

Field of the Invention

The present invention is directed in general to exercise equipment. In one aspect, the present invention relates to an exercise treadmill safety system.

Description of the Related Art

Exercise treadmills provide a moving platform with a wide conveyor belt driven by an electric motor or a flywheel on which a person may perform aerobic-type exercises by walking, jogging, or running in place on the moving platform. Widely used in home, institutional, and commercial settings, such as health clubs, fitness centers and homes, exercise treadmills typically have adjustable settings or controls for adjusting the speed and grade of the platform, and may use a computer-based console having user interfaces to allow a user to view exercise program information and input or select different exercise program information or features. While treadmills provide a great way to improve exercise health, they can, like any high-powered piece of equipment, be dangerous if they are used improperly or safety precautions are not followed. In fact, treadmills are reported to have caused 30 deaths over the ten-year period from 2003-2012, and also cause tens of thousands of injuries each year, many involving children who suffer severe burns on their skin when they accidentally come in contact with a rotating treadmill belt. In addition, injuries in a fitness center or health club can occur when someone unknowingly steps onto an unmanned, rotating treadmill belt or from the interference in the belt speed or elevation of the platform of the machine when an object, such as an exercise ball, comes in contact with the exposed rear portion of the belt.

While there are various treadmill safety systems, such safety systems typically do not prevent serious treadmill injuries from happening. For example, the most prevalent safety system uses a length of cord attached to a stop or kill switch on the treadmill which must be clipped to the user (e.g., at the waist band or shirt of an exerciser), but in order for the kill switch to work, the user must first remember to attach the clip to their clothing at the start of their exercise routine on the treadmill, and even if they do attach the clip, the user's body would have to fall some distance, likely the distance of the length of the cord, for the cord to pull and activate the stop switch. As a result, the user may have already been injured by hitting the moving belt before it stops. Of course, such user activated switches do not protect against someone stepping on a rotating belt on an unmanned treadmill, and offer no safety protection to prevent someone or a pet from being dragged into or under a turning belt on a treadmill. And while there are speed control systems which use sensors (e.g., cameras, sonic, or foot sensors) to adjust the speed of the treadmill conveyor belt based on the detected distance position of the user on the treadmill, such systems can fail to detect that the user has fallen until too late to prevent the user from hitting the moving belt. For example, a treadmill user who falls forward may not be detected if the detected distance position does not change. These same deficiencies apply to optical detector systems which control the treadmill speed based on the detected presence of the user's feet, but do not respond quickly enough to prevent injury. In addition to the deficiencies with existing safety systems in preventing serious injuries to treadmill users, existing treadmill safety systems also fail to protect persons or pets in the vicinity of a treadmill that is in use in a health club and fitness center environment where a row of treadmills is installed with people walking in close proximity to the rear of these treadmills. Accordingly, it can be seen that the existing exercise treadmill systems solutions for providing safety control and protections with exercise treadmills are extremely difficult at a practical level.

BRIEF DESCRIPTION OF THE DRAWINGS

The present invention may be understood, and its numerous objects, features and advantages obtained, when the following detailed description of a preferred embodiment is considered in conjunction with the following drawings.

Figure 1:
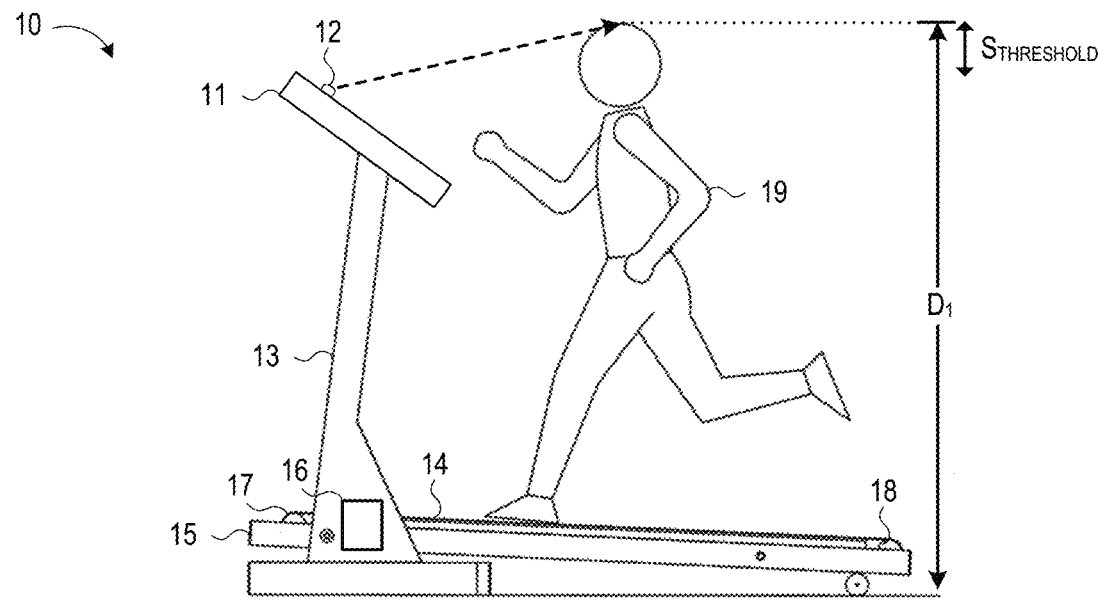
FIG. 1 is a diagrammatic side view of an exercise treadmill safety system for tracking the height of the user running in place in accordance with selected embodiments of the present disclosure.

It will be appreciated that for simplicity and clarity of illustration, elements illustrated in the drawings have not necessarily been drawn to scale. For example, the dimensions of some of the elements are exaggerated relative to other elements for purposes of promoting and improving clarity and understanding.

DETAILED DESCRIPTION

A method, system, and apparatus are described for improving the safety of exercise equipment, such as an exercise treadmill, by autonomously reducing and stopping the treadmill speed upon detecting potential injury events arising when a user falls from the treadmill and when an object or person approaches the treadmill from behind. In selected example embodiments, an autonomous exercise treadmill safety system, method and apparatus may include one or more height sensors for monitoring the height of a treadmill user to detect changes in the height measurement of the user, which may also include determining if the height measurement exceeds a threshold distance, thereby indicating that the user has begun to fall or has stepped off or left the treadmill, at which point the treadmill speed may be reduced and stopped by generating motor control signals to the exercise treadmill. In addition, selected embodiments of the autonomous exercise treadmill safety system, method and apparatus may include one or more rear plane position sensors for monitoring the presence of any object which penetrates a rear sensor plane of the treadmill, at which point the treadmill speed may be reduced and stopped by generating motor control signals to the exercise treadmill. For example, the rear plane position sensors may be implemented with a field of sensors that define a curtain motion sensor at the rear of the treadmill extending some distance above the turning belt and may also extend some distance below the turning belt for detecting the presence of a person or object breaking this plane from the rear and/or detecting a user who has fallen off of the back of the treadmill, causing a control signal to be generated to shut down the treadmill. In selected embodiments, the motor control signals are generated to quickly decelerate the speed of the rotating belt before stopping the belt when the speed of the belt exceeds some predetermined speed. In addition to generating motor control signals, selected embodiments of the autonomous exercise treadmill safety system, method and apparatus may provide a fall detection signal and/or the image of a user who has fallen on a treadmill to a facility monitored by a health club or fitness center so that first aid or emergency medical aid may be promptly provided for the user, if needed.

Various illustrative embodiments of the present invention will now be described in detail with reference to the accompanying figures which illustrate different views of an autonomous exercise treadmill safety system. While various details are set forth in the following description, it will be appreciated that the present invention may be practiced without these specific details, and that numerous implementation-specific decisions may be made to the invention described herein to achieve the device designer's specific goals, such as compliance with mechanical, electrical and/or design-related constraints, which will vary from one implementation to another. While such a development effort might be complex and time-consuming, it would nevertheless be a routine undertaking for those of ordinary skill in the art having the benefit of this disclosure. For example, selected aspects are depicted with reference to simplified plan and perspective views of an exercise treadmill safety system without including every device feature or geometry in order to avoid limiting or obscuring the present invention. Such descriptions and representations are used by those skilled in the art to describe and convey the substance of their work to others skilled in the art.

Figure 2:
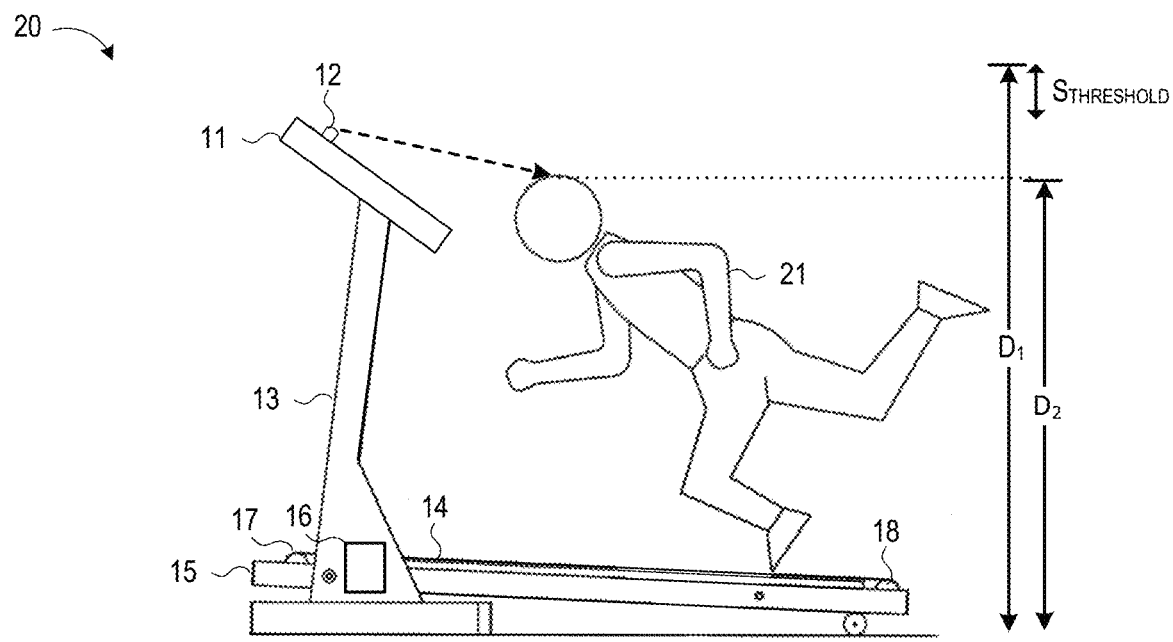
FIG. 2 is a diagrammatic side view of an exercise treadmill safety system for tracking the height of the user who has started to fall in accordance with selected embodiments of the present disclosure.

Turning now to FIGS. 1-2, there are illustrated selected embodiments of an autonomous exercise treadmill safety system, method, and apparatus in which one or more sensors monitor the height of the treadmill user to detect when the user has started to fall and then generate treadmill speed controls to decelerate and stop the treadmill motor. As illustrated in the diagrammatic side view of FIG. 1, the treadmill 10 is shown with a user 19 running on the belt 14 of the treadmill at a time when the treadmill is started. The treadmill belt 14 is a looped belt mounted on a platform housing 15 which includes rollers 17, 18 which are powered by a motor 16. The motor 16 may be housed in a front frame portion 13 of the treadmill 10 which extends to support a control panel 11 which faces the user 19 on the treadmill 10. The control panel 11 houses controls for the user to turn the treadmill 10 "on" and "off," to set the incline and/or speed of the belt 14, and to otherwise provide a user interface to allow the user 19 to view exercise program information and input or select different exercise program information or features. In addition, the control panel 11 may include a sensor 12 for obtaining image data to determine or measure the height D1 of the user 19 as the distance above a predetermined level (e.g., ground) before the motor 16 can apply power to the belt 14. In the illustrated embodiment, the height D1 is the distance from the top of the user's head to the ground surface, but the distance measure could also be made with reference to the surface of the belt 14. By continually monitoring the height of the user 19 in relation to the initial height measurement D1, the sensor(s) 12 may detect if the user's head drops, and in some applications if it drops more than a predetermined threshold distance (e.g., $S_{THRESHOLD}$), so that the belt may be immediately decelerated and stopped.

As will be appreciated, the height detection sensor(s) 12 may use any suitable sensor technology to measure and store the height of the user. For example, the sensor 12 may be embodied as an RGB camera that uses a processor or computer to calculate the height of the user 19 by triangulation. In addition or in the alternative, the sensor 12 may be embodied as a laser measuring device that measures the height of the user 19. The sensor 12 may also include or be a sensing device such as an infrared or 3D depth camera that senses and measures the height of the user as well as the body motion of the user. In whatever sensor technology that is used, the sensor 12 enables a processor or computer to measure the initial height D1 of the user 19 on the treadmill, and to compare the initial height to subsequent height measurements that are made continuously while the user is on the treadmill. If the measured height drops a predetermined threshold distance (e.g., $S_{THRESHOLD}$), this detected condition is transformed by one or more algorithmic rules at the processor or computer to indicate that the user 19 is losing her/his balance and starting to fall, at which time a notification signal is provided to a controller that controls the speed and operation of the motor 16 to decelerate and/or stop the motor from turning the belt 14.

Turning now to FIG. 2, there is shown a diagrammatic side view of the treadmill 20 shown with the user 21 who has started to fall, causing the user's head to drop downward. The sensor 12 continuously captures data to enable the height of the user 21 to be calculated and compared to the initial height D1 in order to detect a "fall" event. If D2 is less than D1, or in some applications if the measured height D2 is more than a predetermined threshold distance (e.g., $S_{THRESHOLD}$) below the initial height D1, then a control signal is generated to either immediately stop the moving belt 14 or to adjust the deceleration and stop the belt 14 in accordance with the speed setting of the treadmill. For example, the control signal may be issued to bring the treadmill belt 14 to an immediate stop in response to a detected fall by the user 21 when the speed is comparable to walking on the treadmill, e.g., 2.0 mph. However, if the user 21 has set the speed to a pace for jogging or running on the treadmill, then the control signal may promptly decelerate the belt 14 if the speed is above a predetermined maximum (e.g., a speed of 2.0 mph which would be associated with walking on the treadmill) before stopping the belt 14 in order to avoid further upsetting the balance of the user 21 by the belt coming to an immediate stop. In addition to generating treadmill speed control signals, a detected fall event may also provide a notification to safety personnel responsible for overseeing or monitoring the safety of patrons of a fitness center or health club, such as by generating an alarm signal along with a visual image of the user who has stumbled or fallen on the treadmill so that the safety personnel may be alerted to assist the patron and, if needed, to provide or call for first aid or emergency medical help. By including the option that the height of the user D2 drops by more than a predetermined threshold distance, the autonomous exercise treadmill safety system avoids generating unnecessary treadmill deceleration and/or stop signals when the user's head drops a small distance that can normally occur during exercise on the treadmill. As one example, the predetermined threshold distance (e.g., $S_{THRESHOLD}$) may be set to be greater than a minimum of one inch or two inches.

Figure 3:
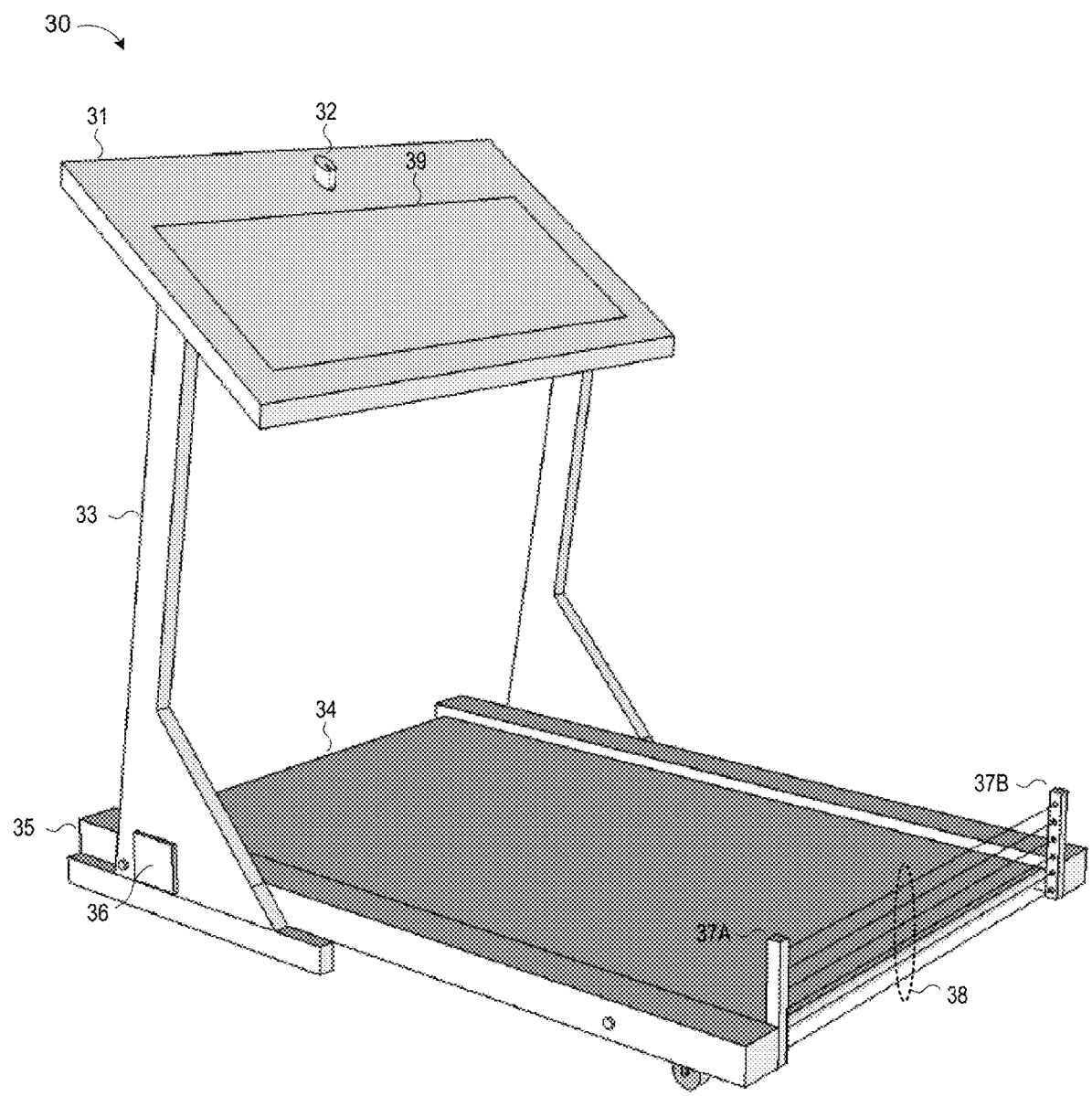
FIG. 3 is a perspective view of an exercise treadmill safety system including a sensor for detecting the height of a user and a field of sensors aligned across the rear plane of the treadmill to stop the treadmill upon detecting that an object has crossed the field of sensors in accordance with selected embodiments of the present disclosure.

To illustrate further embodiments of the autonomous exercise treadmill safety system, method, and apparatus, reference is now made to FIG. 3, which is a perspective view of an exercise treadmill 30 which includes one or more sensors 37A, 37B defining a sensor plane 38 aligned across the rear plane of the treadmill to stop the treadmill upon detecting that an object has crossed the sensor plane 38. As illustrated in FIG. 3, the treadmill 30 includes a treadmill belt 34 that is mounted as a looped belt on a platform housing 35 which includes rollers (not shown) powered by a motor 36 housed in a front frame portion 33 of the treadmill 30 which extends to support a control panel 31. The control panel 31 houses controls (not shown) and an interface 39 for turning the treadmill "on" and "off," setting the incline and/or speed of the belt 34, and/or otherwise providing the user interface 39 for viewing exercise program information and/or inputting or selecting different exercise program information or features. In addition, the control panel 31 may include a sensor 32 for determining or measuring the height of the treadmill user.

As will be appreciated, the sensor(s) 37 may use any suitable sensor technology to define the visible or invisible sensor plane 38 for detecting that an object has crossed the back of the treadmill 30. For example, the sensor(s) 37 may be embodied as a pair of photoelectric sensors 37A, 37B which are positioned and arranged to create a light curtain 38 at the rear of the turning belt 34 which extends above the treadmill belt 34 and which may also extend below the treadmill belt 34. In addition or in the alternative, the sensors 37A, 37B may be configured with separate sending and receiving units to generate the beams of the sensor plane 38, or may be configured with a combined sending/sensing unit and one or more reflectors so that the sensor beams may be operated either in a parallel beam or cross beam mode. The light curtain 38 is illustrated operating in the parallel beam mode. An example of suitable sensors 37A, 37B is the SSXU20 Series Ultra-Thin Light Curtain Sensor, which is switchable between parallel beam and cross beam modes. By including the light curtain 38 to extend below the bottom of the belt 34 as well as a predetermined height above the belt 34, there is provided an autonomous exercise treadmill safety system, method, and apparatus that is suitable for use in the environment of health clubs and fitness centers where people walk behind rows of treadmills, but still provides protection against persons or objects breaking the sensor plane 38 from the rear, such as when a patron is about to step unto a rotating treadmill belt 34 on an unmanned treadmill 30, and/or detecting a user who has fallen off of the back of the treadmill. To further enhance the safety of the exercise treadmill 30, the sensor(s) 37A, 37B may be constructed to retract downward and into the platform frame 35 when the treadmill 30 is not in use. While an invisible light curtain 38 can be used, additional protection for safe treadmill use may be provided by embodying the sensors 37 to generate a visible sensor plane 38 as a "safety net" which alerts persons nearby of the light curtain 38. In whatever sensor plane technology that is used, the sensors 37 would, upon any intrusion of the sensor plane 38 from either the front or back, send an alert signal to the treadmill controller which then generates a control signal to stop the motor 36. As will be appreciated, the disclosed arrangement of sensors 37A, 37B to define a sensor plane 38 can detect and respond to a user falling off of the back of the belt 34 and to an object with penetrates through the light curtain 38 from behind, thereby overcoming problems with prior art systems that broadcast multiple zones in a field or area directly behind the treadmill, and can therefore be erroneously triggered by people walking behind a row of treadmills.

Figure 4:
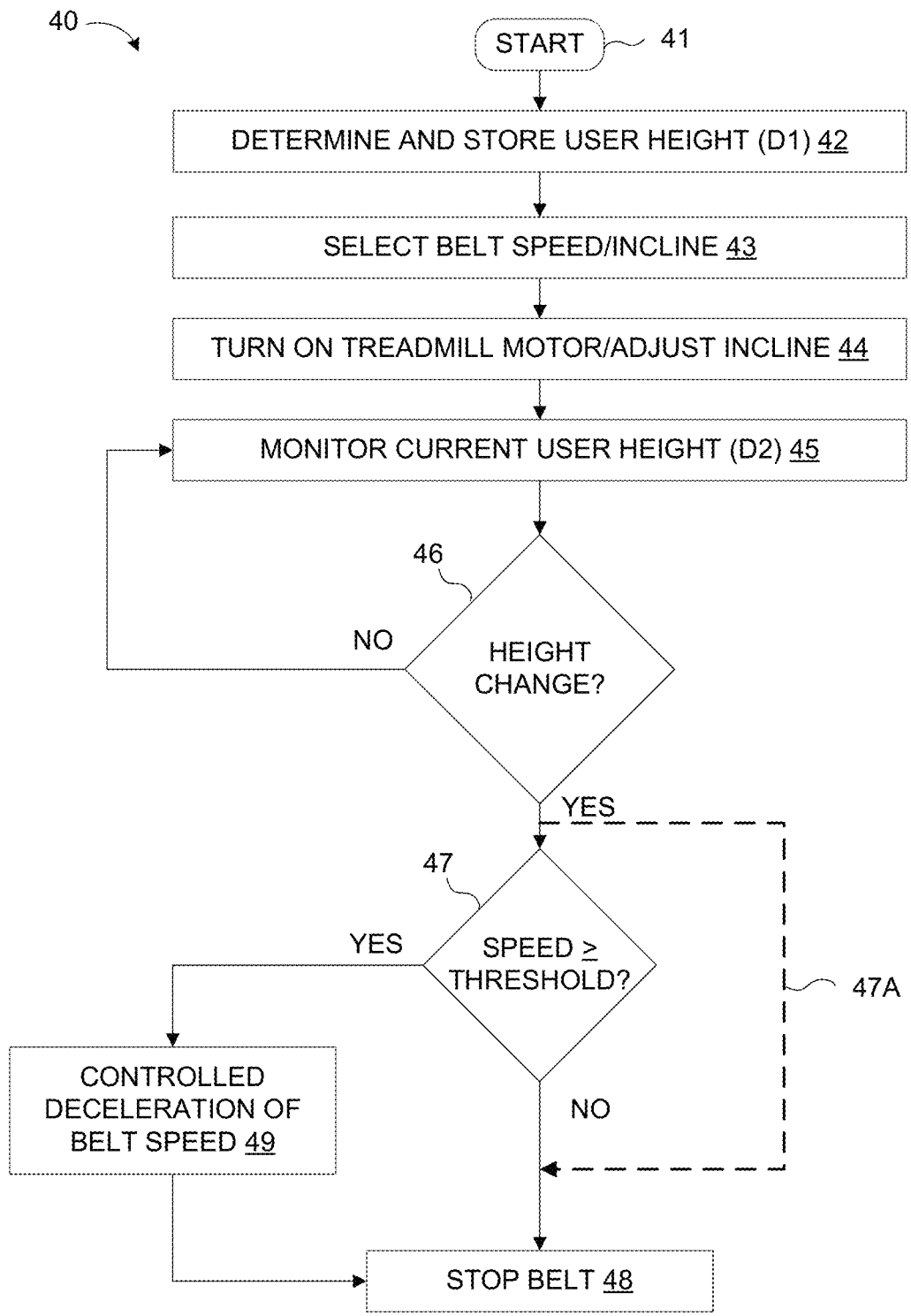
FIG. 4 illustrates a simplified flow chart showing the logic for operating an exercise treadmill safety system in accordance with selected embodiments of the present disclosure.

To provide additional details for an improved understanding of selected embodiments of the present disclosure, reference is now made to FIG. 4 which illustrates a simplified flow chart 40 showing the logic for operating an exercise treadmill safety system in accordance with selected embodiments of the present disclosure. In the depicted flow sequence, the method starts (step 41), such as when the treadmill user presses a "power on" button or similar interface actuator screen on the treadmill control panel.

In step 42, the treadmill safety system calculates or determines an initial height of the user, such as by measuring an initial distance or height (D1) between a point on the user (e.g., the top of the user's head) and a specified level, such as the upper surface of the treadmill belt or a level ground surface. As disclosed herein, any suitable sensor technology and configuration arrangement may be used to measure the user height. For example, the processing at step 42 may be performed by the treadmill safety system which executes control code at a processor which uses one or more height sensors to measure the initial height of the treadmill user. In addition, the processing at step 42 may store the initial height measurement D1 in memory for subsequent use in detecting fall events.

At step 43, the user may select the speed of the treadmill belt and its angle of inclination as part of a system initialization process. In selected embodiments, the system initialization process may be carried out through user interaction with a user interface on the treadmill control panel which is displayed through execution of control code at a processor providing a user interface functionality for specifying treadmill speed and/or incline parameters. Alternatively, the step may be skipped if the user does not specify any requirements for the treadmill speed and incline.

At step 44, the user may turn "on" the treadmill belt by powering up the treadmill motor, such as when the treadmill user presses a "start" button or similar interface actuator screen on the treadmill control panel. In response, the treadmill safety system may execute control code at a processor which responds to the actuated "start" button by issuing a command to the motor controller which powers the belt motor to turn the treadmill belt at the speed and incline specified by the user.

At step 45, the treadmill safety system continuously monitors the height of the treadmill user, such as by measuring a current height (D2) of the treadmill user. Again, any suitable sensor technology and configuration arrangement may be used to continuously measure the user height, including but not limited to executing control code at a processor which uses one or more height sensors to measure the current height of the treadmill user.

At step 46, the treadmill safety system determines if the current height of the treadmill user has changed, including detecting any height change or any height change which exceeds a threshold height change. In selected embodiments, the evaluation at step 46 may be carried out by executing control code at a processor which compares each current height measure (D2) with the initial height measurement (D1) to determine if the head has dropped by more than a threshold distance (e.g., greater than one inch). If the user's head has not dropped by more than the threshold distance, then there is no threshold height change (negative outcome to detection step 46), and the treadmill safety system continues to monitor the current user height (step 45) and the treadmill belt continues to be powered. However, if the user's head does drop by more than the threshold distance then there is a threshold height change (affirmative outcome to detection step 46), at which point the speed of the treadmill belt is adjusted.

In particular, the treadmill safety system may adjust the speed of the treadmill belt by first comparing the current treadmill speed setting selected by the user to a predetermined threshold speed at step 47, where the threshold speed may be a speed associated with walking on the belt (e.g. 2.0 mph). In selected embodiments, the evaluation at step 47 may be carried out by executing control code at a processor which compares the current treadmill speed to the threshold speed for purposes of controlling how quickly the treadmill is decelerated. If the treadmill speed is greater than the threshold speed (affirmative outcome to detection step 47), then the treadmill safety system may first promptly decelerate the treadmill belt speed (step 49) before stopping the treadmill (step 48). However, if the current treadmill speed does not meet or exceed the threshold speed (negative outcome to detection step 47), then the treadmill belt is immediately stopped (step 48).

Figure 5:
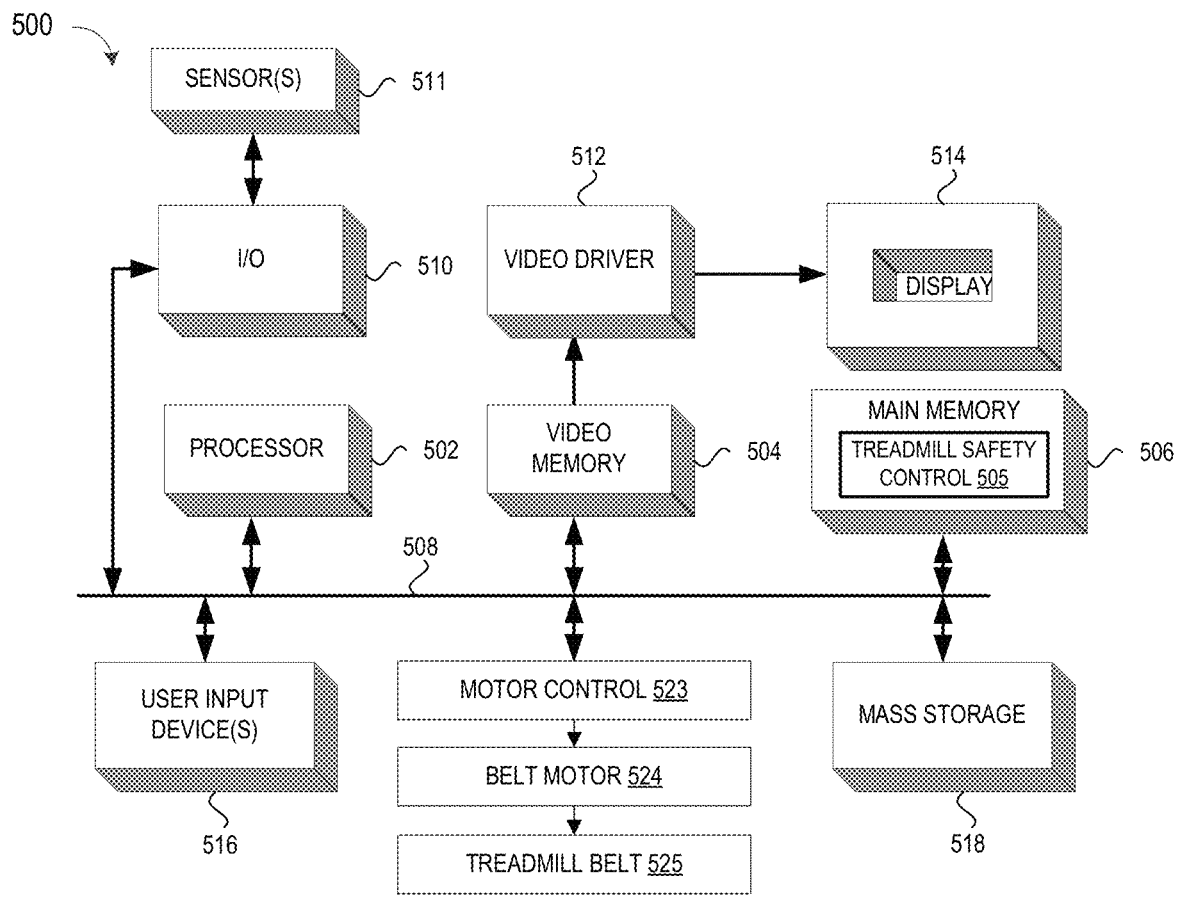
FIG. 5 is a simplified block diagram of an exercise treadmill safety system in accordance with selected embodiments.

Embodiments of the exercise treadmill safety system and method can be implemented on a computer system, such as a general-purpose computer 500 illustrated in FIG. 5. As disclosed the computer 500 includes input user device(s) 516, such as a control panel, keyboard and/or mouse, which are coupled to a bi-directional system bus 508. The input user device(s) 516 are used for introducing user input to the computer system 500 and communicating that user input to processor 502. The computer system 500 may also include a video memory 504, main memory 506, I/O device(s) 510, user input device(s) 516, motor control 523, and mass storage 518, all coupled to bi-directional system bus 508 along with input user device(s) 516 and processor 502. The mass storage 518 may include both fixed and removable media, such as other available mass storage technology. Bus 508 may contain, for example, 32 address lines for addressing video memory 504 or main memory 506. The system bus 508 may also include, for example, an n-bit data bus for transferring data between and among the components, such as CPU 502, main memory 506, video memory 514, and mass storage 518, where "n" is, for example, 32 or 64. Alternatively, multiplex data/address lines may be used instead of separate data and address lines.

The computer 500 also includes one or more I/O device(s) 510 which provide connections to peripheral devices, including one or more sensors 511, such as depth sensors, RGB sensors, and infrared projector height sensors and/or field sensors. The I/O device(s) 510 may also provide a direct connection to remote server computer systems via a telephone link or to the Internet via an ISP, a wireless link, or the like. I/O device(s) 510 may also include a network interface device to provide a direct connection to remote server computer systems via a direct network link to the Internet via a POP (point of presence). Such connection may be made using, for example, wireless techniques, including digital cellular telephone connection, Cellular Digital Packet Data (CDPD) connection, digital satellite data connection or the like. Examples of I/O devices include modems, sound and video devices, and specialized communication devices such as the aforementioned network interface.

Computer programs and data are generally stored as instructions and data in mass storage 518 until loaded into main memory 506 for execution. Computer programs may also be in the form of electronic signals modulated in accordance with the computer program and data communication technology when transferred via a network. The method and functions relating to system and method for providing an autonomous treadmill safety controls may be implemented in a computer program for a treadmill safety control module 505.

The processor 502, in one embodiment, is a microprocessor manufactured by Motorola Inc. of Illinois, Intel Corporation of California, or Advanced Micro Devices of California. However, any other suitable single or multiple microprocessors or microcomputers may be utilized. Main memory 506 is comprised of dynamic random access memory (DRAM). Video memory 504 is a dual-ported video random access memory. One port of the video memory 504 is coupled to video amplifier or driver 512. The video amplifier 512 is used to drive the display 514. Video amplifier 512 is well known in the art and may be implemented by any suitable means. This circuitry converts pixel data stored in video memory 504 to a raster signal suitable for use by display 514. Display 514 is a type of monitor suitable for displaying graphic images.

Under control of the processor(s) 502, the principal hardware elements of the exercise treadmill safety system include the motor control 523 and belt motor 524 which control the speed of treadmill belt 525 in response to fall events detected by the sensor(s) 511. For example, a first sensor 511 may be provided to capture images of the user of the treadmill and to provide sensor data over the I/O device(s) 510 to the processor(s) 502 for storage and/or processing to calculate the height of the top of the user's head. In selected embodiments where the sensor 511 is embodied as an RGB camera, the processor(s) 502 may execute instructions from the treadmill safety control module 505 which calculate triangulation measurements to measure the initial user height (D1) and/or current user height (D2). One such approach for measuring the height of people or objects is found in the EasyMeasure app for an iPhone's RGB camera. In other embodiments, the sensor 511 could be embodied as a laser device which calculates the user height, such as by using an LTI laser rangefinder that includes a tilt sensor to calculate height with a three shot routine, where the first shot establishes the horizontal distance to the user, and then the second and third shots determine the top and base angles. The height of the user is then calculated with this data. In other embodiments, other types of technology could be used for the sensor(s) 511, such as a depth camera with depth sensors, an RGB sensor, and infrared projector to determine the height and even the body motion of the user. One such depth camera is the Intel RealSense™ Depth Camera D400-series.

In operation, the computer system 500 may be configured to process the data generated by the sensor(s) 511 with the processor(s) 502 to determine the initial height D1 of the user before the treadmill belt 525 is started in motion. After measuring the initial height, the sensor(s) 511 continue to generate data and enables the processor(s) 502 to execute instructions from the treadmill safety control module 505 to determine the present height (D2) of the user on the treadmill belt 525. If the current height measurement D2 changes from the initial height measurement (D1) or is below the initial height (D1) by at least a predetermined threshold distance X, then the processor(s) 502 execute instructions from the treadmill safety control module 505 to generate a control signal to the motor controller 523 to cause the motor 524 to either immediately stop the belt 525, or to first decelerate and then stop the belt 525 if the treadmill speed exceeds a predetermined speed threshold. The predetermined threshold distance X should be of a sufficient value to avoid unnecessary and unwanted "false" fall signals when the user head moves down some small distance in the normal course of using a treadmill. As an example, the predetermined threshold distance X could be set into the program control of the treadmill safety control module 505 as a value of one inch or two inches or more.

Figure 6:
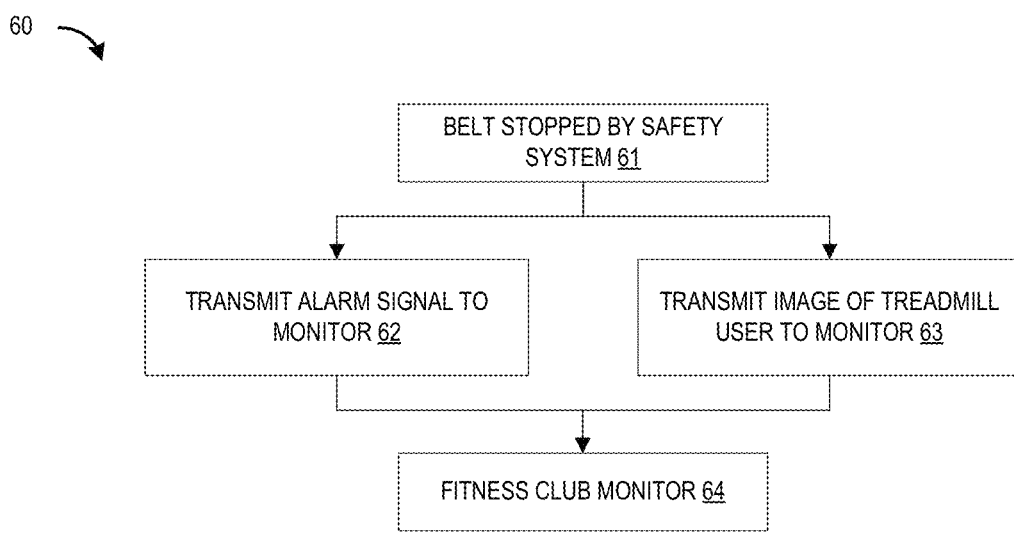
FIG. 6 illustrates a simplified flow chart showing the logic for notifying a fitness club monitor system if a belt stoppage occurs in accordance with selected embodiments of the present disclosure.

To provide additional details for an improved understanding of selected embodiments of the present disclosure, reference is now made to FIG. 6 which illustrates a simplified flow chart 40 showing the logic for notifying a fitness club monitor system if a belt stoppage occurs, such as when detecting that a treadmill user is starting to fall on a treadmill or when an object penetrates a field sensor array on the back of the treadmill. Upon stoppage of the belt at step 61, the treadmill safety system may transmit an alarm signal(s) (step 62) to a monitoring station/system (step 64) maintained by a health club or fitness center. In addition, the treadmill safety system may transmit an image of the treadmill user (step 63) to the monitoring station/system (step 64). The alarm signal from the treadmill may be used to generate an appropriate audio and/or visual signal to alert the health club or fitness center that a patron has fallen on a treadmill. In addition, the sensor(s) 511 may transmit an image of the treadmill user. By including such an alarm system as part of the autonomous safety system, first aid and medical attention can be provided to patrons of health clubs or fitness centers who have experienced a fall, if needed.

By now, it should be appreciated that there has been provided an apparatus, method, program code, and system for controlling the operation of an exercise treadmill with an autonomous treadmill safety system. In the disclosed embodiments, a treadmill motor is prevented from starting to move the treadmill belt until an initial height to the treadmill user on the treadmill belt is measured and stored. When measuring the initial height of the treadmill user, the system may measure a topmost point on the user's head in relation to point on a surface of treadmill belt (or a point on a surface on which the exercise treadmill rests) in any suitable way. In selected embodiments, the initial height is measured from an image collected by an RGB camera sensor, or may be measured with a laser rangefinder device or depth camera. Once the initial height is measured, a treadmill motor is enabled to start moving the treadmill belt. While the treadmill belt is moving, a current height of the treadmill user is measured for evaluation against the initial height. For example, the current height may be periodically (or "continuously") measured while the treadmill is in use using any suitable height detection technique. At any point when the current height is lower than the initial height (which could in some applications be detected as being lower by a predetermined distance), a first treadmill motor control signal is generated to stop the treadmill motor from moving the treadmill belt. In selected embodiments, the treadmill motor is stopped immediately without checking the speed (as indicated with the dashed line 47A). In other embodiments, the treadmill motor is stopped by first comparing a current speed of the treadmill belt to a predetermined maximum speed, decelerating the current speed of treadmill belt to a specified slower speed in response to the first treadmill motor control signal if the current speed exceeds the predetermined maximum speed, and then stopping the treadmill belt after the treadmill belt reaches the specified slower speed. In other disclosed embodiments, the apparatus, method, program code, and system control the operation of an exercise treadmill by first generating a field sensor plane at a rear portion of the treadmill belt or treadmill frame structure to detect any object which penetrates the field sensor plane, and then generating a second treadmill motor control signal when an object penetrates the field sensor plane, where the treadmill motor stops the treadmill belt from moving in response to the second treadmill motor control signal. In selected embodiments, the field sensor plane may be generated as light current sensor with a plurality of light current sensor devices which are positioned on sensor poles affixed to the rear portion of the treadmill belt. In other embodiments, the field sensor plane is generated to extend above and below the treadmill belt.

In another form, there is provided an exercise treadmill apparatus, method, program code, and system. In the disclosed embodiments, the exercise treadmill includes a frame structure for housing a treadmill motor driving a treadmill belt. The exercise treadmill also includes one or more height sensors (e.g., RGB camera sensors, laser rangefinder devices, or depth camera.) connected to the frame structure for making height measurements of a treadmill user. In addition, the exercise treadmill includes a control system operatively connected to said treadmill motor and one or more height sensors for evaluating an initial height measurement of the treadmill user against one or more subsequent height measurements of the treadmill user taken during operation of the exercise treadmill by the treadmill user to generate a treadmill motor control signal for stopping the treadmill motor when a subsequent height measurement is lower than the initial height measurement. For example, the control system may be configured to generate the treadmill motor control signal when the current height is lower than the initial height by a minimum height threshold distance, such as a distance of 1-2 inches. In selected embodiments, the control system and height sensors are configured to make the initial height measurement by measuring a topmost point on the user's head in relation to a point on a surface of treadmill belt or on a surface on which the exercise treadmill rests. In selected embodiments, the control system is configured to stop the treadmill motor by comparing a current speed of the treadmill belt to a predetermined maximum speed; decelerating the current speed of treadmill belt to a specified slower speed in response to the treadmill motor control signal if the current speed exceeds the predetermined maximum speed; and stopping the treadmill belt after the treadmill belt reaches the specified slower speed. In other embodiments, the control system is configured to stop the treadmill motor by comparing a current speed of the treadmill belt to a predetermined maximum speed; and stopping the treadmill belt in response to the treadmill motor control signal if the current speed does not exceed the predetermined maximum speed. The exercise treadmill may also include one or more light current sensor devices connected to the frame structure for generating a field sensor plane at a rear portion of the treadmill belt, where the control system is connected to the one or more light current sensor devices to detect any object penetration of the field sensor plane. In such embodiments, the light current sensor devices may be arranged to generate the field sensor plane to extend above and below the treadmill belt.

In yet another form, there is provided a treadmill fall detection system, method, program code, and apparatus. In the disclosed embodiments, the treadmill fall detection system includes a treadmill having a treadmill motor driving a treadmill belt. The treadmill fall detection system also includes one or more sensors connected to the treadmill for making height measurements of a treadmill user, where the one or more sensors are selected from a group consisting of an RGB camera sensor, a laser rangefinder device, and a depth camera sensor. In addition, the treadmill fall detection system includes one or more light current sensor devices connected to the treadmill for generating a field sensor plane which extends above a rear portion of the treadmill belt and may also include extending the sensor plane some distance below the treadmill belt. Finally, the treadmill fall detection system includes a processor that executes control instructions to generate one or more treadmill motor control signals for decelerating and stopping the treadmill motor. In particular, the control instructions are executed to calculate the height measurements of the treadmill user based on sensor data provided by the one or more sensors and to evaluate an initial height measurement of the treadmill user against one or more subsequent height measurements of the treadmill user taken during operation of the exercise treadmill by the treadmill user to generate a first treadmill motor control signal for stopping the treadmill motor if a subsequent height measurement drops a predetermined distance from the initial height measurement. In addition, the control instructions are executed to monitor sensor data provided by the one or more light current sensor devices to generate a second treadmill motor control signal for stopping the treadmill motor upon detecting any object penetration of the field sensor plane.

While the invention has been described in connection with what is presently considered to be the most practical and preferred embodiment, it will be appreciated that other variations and alternatives to the disclosed examples are also contemplated, and the present invention is not necessarily limited to the example embodiments, which illustrate inventive aspects of the present invention that are applicable to various exercise equipment applications. For example, other sensors technologies may be used to detect a user fall event early during the actual fall. In addition, the ability to detect user fall events may be used with other types of exercise equipment. Thus, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law. Accordingly, the foregoing description is not intended to limit the invention to the particular form set forth, but on the contrary, is intended to cover such alternatives, modifications and equivalents as may be included within the spirit and scope of the invention as defined by the appended claims so that those skilled in the art should understand that they can make various changes, substitutions and alterations without departing from the spirit and scope of the invention in its broadest form.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. The term "coupled," as used herein, is not intended to be limited to a direct coupling or a mechanical coupling. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method for operating an exercise treadmill, comprising:
    measuring an initial height of a user standing on a stationary treadmill belt before the treadmill belt is started in motion;
    saving the initial height in memory;
    enabling a treadmill motor to start moving the treadmill belt only after measuring the initial height of the user;
    continuously measuring a current height of the user on a moving treadmill belt as a distance from a top of a head of the user on the moving treadmill belt to a surface of the moving treadmill belt;
    evaluating the current height against the initial height to detect when the current height is lower than the initial height by a minimum threshold distance of 1-2 inches, thereby generating a first treadmill motor control signal for stopping the treadmill belt when the user is starting to fall and (a) before the user has fallen onto or off of the moving treadmill belt or (b) before the user moves to the back of the moving treadmill belt; and
    stopping the treadmill motor from moving the treadmill belt in response to the first treadmill motor control signal.

2. The method of claim 1, where measuring the initial height comprises measuring the initial height of the user from an image collected by an RGB camera sensor.

3. The method of claim 1, where measuring the initial height comprises measuring the initial height of the user with a laser rangefinder device.

4. The method of claim 1, where measuring the initial height comprises measuring the initial height of the user with a depth camera.

5. The method of claim 1, where continuously measuring the current height comprises periodically measuring the current height of the user while the treadmill is in use.

6. The method of claim 1, where stopping the treadmill motor comprises:
    comparing a current speed of the treadmill belt to a predetermined maximum speed;
    decelerating the current speed of treadmill belt to a specified slower speed in response to the first treadmill motor control signal if the current speed exceeds the predetermined maximum speed; and
    stopping the treadmill belt after the treadmill belt reaches the specified slower speed.

7. An exercise treadmill, comprising:
    a frame structure for housing a treadmill motor driving a treadmill belt;
    one or more height sensors connected to the frame structure for making height measurements of a treadmill user; and
    a control system, operatively connected to said treadmill motor and one or more height sensors, configured to evaluate an initial height measurement of the treadmill user on the stationary treadmill belt before the treadmill belt is started in motion against one or more subsequent height measurements of the treadmill user on the moving treadmill belt taken during operation of the exercise treadmill and generate a treadmill motor control signal for stopping the treadmill motor when a subsequent height measurement of one or more subsequent height measurements is lower than the initial height measurement by a predetermined threshold distance of 1-2 inches so that the treadmill belt is stopped when the user is starting to fall and (a) before the user has fallen onto or off of the moving treadmill belt or (b) before the user moves to the back of the moving treadmill belt, wherein the treadmill belt is configured to start in motion only after the initial height measurement is measured.

8. The exercise treadmill of claim 7, where the control system and one or more height sensors are configured to make the initial height measurement by measuring a topmost point on a head of the treadmill user standing on the stationary treadmill belt in relation to a point on a surface of treadmill belt or on a surface on which the exercise treadmill rests.

9. The exercise treadmill of claim 7, where the one or more height sensors comprise one or more RGB camera sensors, laser rangefinder devices, or depth cameras.

10. The exercise treadmill of claim 7, where the control system is configured to stop the treadmill motor by:
   comparing a current speed of the treadmill belt to a predetermined maximum speed;
   decelerating the current speed of treadmill belt to a specified slower speed in response to the treadmill motor control signal if the current speed exceeds the predetermined maximum speed; and
   stopping the treadmill belt after the treadmill belt reaches the specified slower speed.

11. The exercise treadmill of claim 7, where the control system is configured to stop the treadmill motor by:
   comparing a current speed of the treadmill belt to a predetermined maximum speed; and
   stopping the treadmill belt in response to the treadmill motor control signal if the current speed does not exceed the predetermined maximum speed.

12. A method for operating an exercise treadmill, comprising:
   determining an initial distance from a top of a head of a user standing on a stationary treadmill belt of the exercise treadmill to a surface of the stationary treadmill belt before the treadmill motor starts to move the treadmill belt;
   saving the initial distance from the top of the head of the user to the surface of the treadmill belt;
   enabling a treadmill motor to start moving the treadmill belt only after determining the initial distance;
   continuously determining a current distance from the top of the head of the user on a moving treadmill belt to the surface of the moving treadmill belt;
   comparing the saved initial distance to the current distance to determine when the user first starts to fall;
   generating a first treadmill motor control signal to stop the treadmill motor when the current distance from the top of the head of the user to the moving treadmill belt is lower than the saved initial distance by a predetermined threshold distance so that the treadmill belt may be stopped when the user is starting to fall and (a) before the user has fallen onto or off of the moving treadmill belt or (b) before the user moves to the back of the moving treadmill belt.

13. The method of claim 12, where the predetermined threshold distance is one to two inches.

14. The method of claim 12, where the predetermined threshold distance is greater than a minimum of two inches.

15. A method for operating an exercise treadmill, comprising:
   powering on the exercise treadmill without applying power to a treadmill motor so that a treadmill belt is not moving;
   measuring an initial distance from a top of a head of a user standing on the treadmill belt to a surface of the treadmill belt that is not moving;
   saving the initial distance from the top of the head of the user to the surface of the treadmill belt;
   turning on the treadmill motor so that the treadmill belt is moving, wherein the treadmill motor is enabled to move the treadmill belt only after the initial distance is measured;
   measuring a current distance from the top of the head of the user to the surface of the moving treadmill belt while the treadmill belt is moving;
   evaluating the current distance against the initial distance to detect when the current distance has dropped by a minimum threshold distance from the initial distance, thereby generating a treadmill motor control signal for stopping the treadmill belt when the user is starting to fall and (a) before the user has fallen onto or off of the moving treadmill belt or (b) before the user moves to the back of the moving treadmill belt; and
   stopping the exercise treadmill in response to the treadmill motor control signal.

16. The method of claim 15, where the minimum height threshold distance is one to two inches.

* * * * *